US006509032B1

(12) United States Patent
Huang et al.

(10) Patent No.: US 6,509,032 B1
(45) Date of Patent: *Jan. 21, 2003

(54) CATIONIC AMPHIPHILES

(75) Inventors: Leaf Huang, Wexford, PA (US); Richard M. Epand, Hamilton (CA); Remo Bottega, Ancaster (CA)

(73) Assignee: McMaster University, Hamilton (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/382,893

(22) Filed: Feb. 2, 1995

Related U.S. Application Data

(60) Division of application No. 08/189,594, filed on Jan. 31, 1994, now abandoned, which is a continuation-in-part of application No. 07/751,873, filed on Aug. 28, 1991, now Pat. No. 5,283,185.

(51) Int. Cl.$^7$ .............................. A61K 9/127; C07J 9/00
(52) U.S. Cl. ...................... 424/450; 935/54; 552/544
(58) Field of Search ...................... 424/450, 1.21, 424/9.321, 9.51, 417, 94.3; 428/402.2; 935/54; 552/544; 436/829

(56) References Cited

U.S. PATENT DOCUMENTS

| | | |
|---|---|---|
| 4,544,545 A | 10/1985 | Ryan et al. |
| 4,897,355 A | 1/1990 | Eppstein et al. |
| 4,958,013 A | 9/1990 | Letsinger |
| 5,100,662 A | 3/1992 | Bolcsak et al. |

FOREIGN PATENT DOCUMENTS

EP          394111          10/1990

OTHER PUBLICATIONS

Leventis, et al., *Chem. Abs.*, vol. 113, Jul. 1990, Abstract No. 20466.

Leventis, et al., "Interactions of Mammalian Cells with Lipid Dispersions Containing Novel Metabolizable Cationic Amphiphiles", *Biochim. Biophys. Acta.*, vol. 1023, pp. 124–132 (1990).

Phillips, et al. from *Liposomes as Drug Carriers*, John Wiley & Sons, 1988, G. Gregoriadis, et., pp. 243–259.

P. L. Felgner and G. M. Ringold, "Cationic Liposome–Mediated Transfection", *Nature*, vol. 337, pp. 387–388 (1989).

Felgner, et al., "Lipofection: A Highly Efficient, Lipid–Mediated DNA–Transfection Procedure", *Proc. Natl. Acad. Sci. U.S.A*, vol. 84, pp. 7413–7417 (1987).

(List continued on next page.)

*Primary Examiner*—Gollamudi S. Kishore

(57) ABSTRACT

A cationic lipid useful in transfection of cells with DNA is disclosed.

30 Claims, 6 Drawing Sheets

OTHER PUBLICATIONS

Ito, et al., "Synthetic Cationic Amphiphiles for Liposome-Mediated DNA Transfection", *Biochem. Intern.*, vol. 22(2), pp. 235–241 (1990).

Pinnaduwage, et al., "Use of a Quanternary Ammonium Detergent in Liposome Mediated DNA Transfection of Moure L–Cells", *Biochem. Biophys. Acta*, vol. 985, pp. 33–37 (1989).

Mueller, et al., "Laboratory Methods Efficient Transfection adn expression of Heterologous Genes in PC12 Cells", *DNA and Cell Biol*, vol. 9(3), pp. 221–229 (1990).

Stamatatos, L., Leventis, R., Zuckerman, M.J., and Silvius, J.R., "Interactions of Cationic Lipid Vesicles with Negatively Charged Phospholipid Vesicles and Biological Membranes", *Biochemistry*, 27:3917–3925 (1988).

Cheetham, J. J., et al., "Cholesterol Sulfate Inhibits the Fusion of Sendai Virus to Biological and Model Membrane", *Journal of Biological Chemistry*, vol. 265, No. 21, pp. 12404–12409 (1990).

Letsinger, R. L., et al., "Cholesteryl–conjugated Oligonucleotides: Synthesis, Properties and Activity as Inhibitors of Replication of Human Immunodeficiency Virus in Cell Culture", *Proc. Natl. Acad. Sci. USA*, (1989).

Rose, J. K., et al., "A New Cationic Liposome Reagent Mediating Nearly Quantitative Transfection of Animal Cells", *BioTechniques*, vol. 10, No. 4, pp. 520–525 (1991).

Behr, J.P., et al, "Efficient gene transfer into mammalian primary endocrine cells with lipopolyamine–coated DNA", Proceedings of the National Academy of Sciences, USA, 86, 1989, pp. 6982–6986.

Epand, R.M., "The relationship between the effect of drugs on bilayer stability and on protein kinase C activity", Chem–Biol. Interactions, 63, 1987, pp. 239–247.

Felgner, P.L., "Particulate systems and polymers for the in vitro and in vivo delivery of polynucleotides", Advanced Drug Delivery Reviews, 5, 1990, pp. 163–187.

Hannun, Y.A. et al, "Sphingosine inhibition of protein kinase C activity and phorbol dibutyrate binding in vitro and in human platelets", Journal of Biological Chemistry, 261, 1986, pp. 12604–12609.

Loeffler, J.P., et al, "Lipopolyamine–mediated transfection allows gene expression studies in primary neuronal cells", Journal of Neurochemistry, 54(5), 1990, pp. 1812–1815.

CATIONIC AMPHIPHILES

RELATED CASE

This is a division of application Ser. No. 08/189,594, filed Jan. 31, 1994, now abandoned, which is in turn a continuation-in-part of application Ser. No. 07/751,873, filed Aug. 28, 1991, now U.S. Pat. No. 5,283,185.

BACKGROUND OF THE INVENTION

The present invention relates to methods for facilitating the transfer of nucleic acids into cells and to a novel cationic amphiphile useful for this purpose.

Some but not all cationic amphiphiles are known to facilitate the transfer of DNA into cells, i.e., transfection. Although the mechanism of this activity is not yet clear, it probably involves the binding of the DNA/lipid complex with the cell surface via the excess positive charges on the complex. Cell surface bound complex is probably internalized and the DNA is released into the cytoplasm of the cell from an endocytic compartment. How the released DNA moves into the nucleus is not known.

A cationic amphiphile contains the following four important structural elements:

lipophilic group, - - - Linker bond, - - - Spacer arm, - - - Amino group

The amino group is positively charged at neutral pH. It may be a primary, secondary, tertiary or quaternary ammonium group. The spacer arm is usually a hydrophilic, 2 to 15-atom moiety which connects the amino group to the lipophilic group via the linker bond. The linker bond is either an ether, ester, amide or other hydrolyzable bond.

The lipophilic group is a hydrophobic moiety which allows the insertion of the cationic amphiphile into the membranes of the cell or liposome. It serves as an anchor for the cationic ammonium group to attach to the surface of a cell or liposome.

N-[1-(2,3-dioleoxyloxy)propyl]-N,N,N-trimethyl ammonium chloride (DOTMA) is the first cationic amphiphile exhibiting the activity of transfection. Its lipophilic group is a double-chain, C18:1 aliphatic group. It contains a quaternary ammonium group connected to the lipophilic group via a 3-carbon spacer arm with two ether linker bonds. Although the molecule is effective in transfection, it is not biodegradable and is rather toxic to cells.

Another series of cationic amphiphiles used in transfection on is the quaternary ammonium detergents. Either single chain (such as cetyltrimethylammonium bromide) or double chain (such as dimethyldioctadecylammonium bromide) detergents exhibit activity to transfect animal cells. The amino group in these amphiphiles is quaternary and is connected to the lipophilic group without the spacer arm or linker bonds. Another single-chain detergent, stearylamine, contains a primary amino group connected to a single C18:0 chain without a spacer arm or linker bond. This group of amphiphiles is also toxic to the cells.

Two other groups of cationic amphiphiles for transfection have been reported. The first group contains two C18:1 chains as the lipophilic group. The second group contains a cholesterol moiety as the lipophilic group. Both groups contain a quaternary ammonium group, but the spacer arm structure varies. In one case, the trimethylammonium group is directly connected to the two C18:1 chains via a 3-carbon spacer arm and ester bond. The amphiphile, 1,2-dioleoxy-3-(trimethylammonio)propane, (DOTAP) is a close analog of DOTMA. In other cases, such as 1,2-dioleoyl-3-(4'-trimethylammonio)butanoyl-sn-glycerol, DOBT, or cholesteryl(4'-trimethylammonio)butonate, ChOTB, the trimethyl-ammonium group is connected via a butanoyl spacer arm to either the double-chain (for DOTB) or cholesteryl (for ChOTB) group. Other amphiphiles, i.e., 1,2-dioleoyl-3-succinyl-sn-glycerol choline ester (DOSC) and cholesteryl hemisuccinate choline ester, ChOSC, contain a choline moiety as the quaternary ammonium group which is connected to the double-chain (for DOSC) or cholesteryl (for ChOSC) group via a succinyl spacer arm. The transfection activities of these amphiphiles are generally weak.

Yet another class of amphiphiles, called "lipopolyamine" has also been reported. The ammonium group is L-5-carboxyspermine which contains 2 primary and 2 secondary ammonium groups. Two examples of this lipopolyamine are dioctadecyl amidologlycylspermine, DOGS, and dipalmitoyl phosphatidylethanolamidospermine, DPPES. The cationic group is connected to two different double-chain, C16:0 lipophilic group via an amidoglycyl (for DOGS) or phosphorylethanolamine (for DPPES) spacer arm. These compounds are especially efficient in transfecting the primary endocrine cells without cellular toxicity.

A lipopolylysine reagent for transfection has also been reported. The reagent contains a polylysine moiety as the ammonium group which is connected to a phospholipid (N-glutarylphosphatidylethanolamine). Therefore, the spacer arm is the side chain of lysine and the head group of the phospholipid. The lipophilic group is a double-chain, C18:1 group connecting to the spacer arm via two ester bonds. Although the reagent is efficient in transfection and non-toxic to cells, the activity requires scraping the treated cells. This is clearly not a convenient step and cannot be done for in vivo experiments.

An ideal transfection reagent should exhibit a high level of transfection activity without scraping or any other mechanical or physical manipulations of the cells or tissues. The reagent should be non-toxic or minimally toxic at the effective doses. It should also be biodegradable to avoid any long-term adverse side-effects on the treated cells.

Many reagents which fulfill these criteria contain a linker bond that is hydrolyzable in the cell. For example, DOBT and DOSC, both contain ester linker bonds, can be metabolized and catabolized into other lipid species in the treated cells. However, cationic amphiphiles containing ester linker bonds are not stable when stored in an aqueous solution. This is probably due to a base-catalyzed hydrolysis reaction mediated by the amino group of the amphiphile.

Another key factor on the cellular toxicity of the cationic amphiphiles is their inhibitory effects on the activity of protein kinase C (PKC). PKC is a key enzyme which plays a crucial role in cellular signal transduction. Cationic amphiphiles inhibit PKC activity by mimicking the endogenous inhibitor, sphingosine. PKC activity is also important for the cellular endocytosis pathway which is likely to be involved in the action of the cationic amphiphiles to facilitate the entry of DNA into cells. Recently it has been reported that a PKC activator, phorbolmyristateacetate, can stimulate the transfection efficiency of DNA mediated by the calcium phosphate precipitates.

SUMMARY OF THE INVENTION

The present inventors have therefore synthesized a series of novel cationic amphiphiles and screened their activities to inhibit PKC. Several amphiphiles which exhibit weak inhibitory activities towards PKC are particularly suitable for transfections. In addition, there has been prepared cationic reagents with a carbamoyl linker bond in order to overcome the problem of instability in solution. The stability of the bond in aqueous solution is much greater than that of the ester bond, yet it is hydrolyzable in the cell.

In brief, the present invention provides a method for facilitating the transfer of nucleic acids into cells. The method comprises preparing a mixed lipid dispersion of a cationic lipid with a co-lipid in a suitable carrier solvent, such as distilled water or normal saline solution. The cationic lipid has a structure which includes a lipophilic group derived from cholesterol, a linker bond, a spacer arm including a moiety of 1 to about 20 atoms, usually alkyl of 1 to 6 carbon atoms, in a branched or unbranched linear alkyl chain, and a cationic amino group. The amino group is selected from the group consisting of primary, secondary, tertiary and quaternary amino groups. The method further comprises adding the nucleic acids to the dispersion to form a complex. The cells are then treated with the complex.

In a preferred embodiment of the invention, the dispersion has particles with an average diameter of about 150nm. The cationic lipid is preferentially selected from the group consisting of cholesteryl-3β-carboxyl-amidoethylenetrimethylammonium iodide, 1-dimethylamino-3-trimethylammonio-DL-2-propyl-cholesteryl carboxylate iodide, cholesteryl-3β-carboxyamidoethyleneamine, cholesteryl-3β-oxysuccinamidoethylenetrimethylammonium iodide, 1-dimethylamino-3-trimethylammonio-DL-2-propyl-cholesteryl-3β-oxysuccinate iodide, 2-[(2-trimethylammonio)-ethylmethylamino]ethyl-cholesteryl-3β-oxysuccinate iodide, 3β[N-(N',N'-dimethylaminoethane)-carbamoyl]cholesterol, and 3β-[N-(polyethyleneimine)-carbamoyl]cholesterol.

In a preferred embodiment, the co-lipid is a neutral or acidic phospholipid which may be preferentially selected from the group consisting of phosphatidyl choline and phosphatidyl ethanolamine.

In addition, the present invention also provides a substantially non-toxic,substantially non-hydrolyzable cationic lipid for facilitating the transfer of nucleic acids into cells. The lipid comprises a lipophilic group derived from cholesterol, a linker bond, a spacer arm including from about 1 to about 20 carbon atoms, preferably 1 to 6 carbon atoms in a branched or unbranched linear alkyl chain, and a cationic amino group. The amino group is selected from the group comprising primary, secondary, tertiary or quaternary amino groups.

The cationic lipid is preferably selected from the group consisting of cholesteryl-3β-carboxyamidoethylenetrimethylammonium iodide, 1-dimethylamino-3-trimethylammonio-DL-2-propyl-cholesteryl carboxylate iodide, cholesteryl-3β-carboxyamidoethyleneamine, cholesteryl-3β-oxysuccinamidoethylenetrimethylammonium iodide, 1-dimethylamino-3-trimethylammonio-DL-2-propyl-cholesteryl-3β-oxysuccinate iodide, 2-[(2-trimethylammonio)-ethylmethylamino]ethyl-cholesteryl-3β-oxysuccinateiodide, 3β[N-(N',N'dimethylaminoethane)-carbamoyl]-cholesterol, and 3β[N-(polyethyleneimine)-carbamoyl]cholesterol.

BRIEF DESCRIPTION OF THE DRAWINGS

The present invention may be better understood by reference to the following Examples when considered in conjunction with the drawings in which.

DETAILED DESCRIPTION OF PREFERRED EMBODIMENTS

Figure 1:
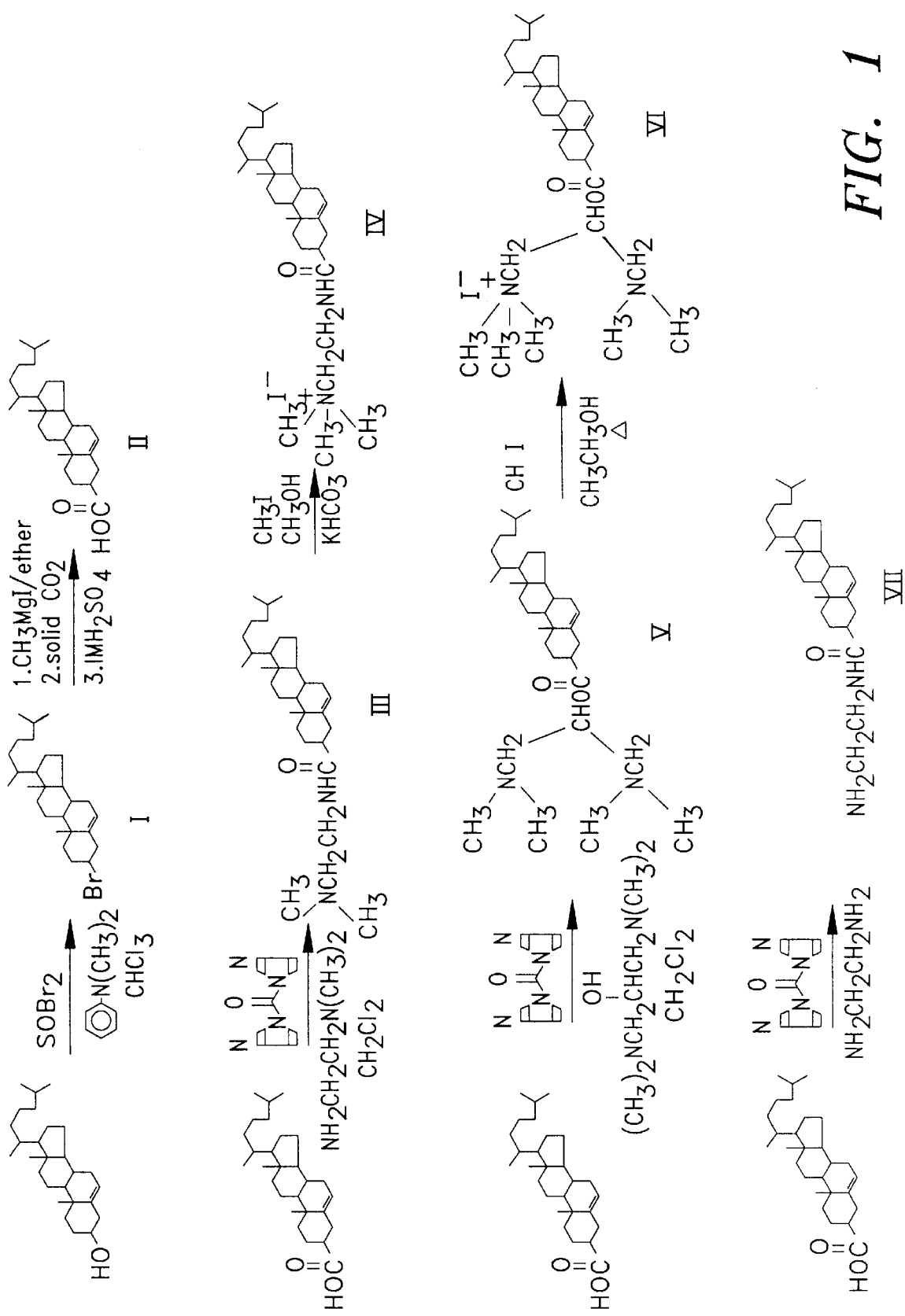
FIG. 1 is the synthetic scheme for cholesteryl carboxylate analogues.

When used in gene therapy, the dispersions of the invention containing at least one cationic lipid of the invention may be used to deliver DNA into the selected eukaryotic cell. Protocols for stable transformation and expression of DNA integrated into the genome of the transfected cell are known. Typical protocols for liposome-mediated transfections are described in Ausebel et al. *Current Protocols in Molecular Biology*, Volume 1, Unit 9.4.1 and, also generaly, see Chapter 9 for Introduction of DNA into Mammalian Cells.

The dispersions of the invention can also be used to introduce nucleic acid, e.g. plasmid DNA into protoplasts of prokaryotic cells by methods known in the art.

The dispersions of the invention can be used to introduce nucleic acids into protoplasts of plant cells. Phospho-lipids vesicles have been used for intracellular delivery of liposomal contents into plant cells in reported work with tobacco protoplasts. Tobacco mosaic virus (TMV), RNA has been encapsulated in liposome preparations using the reverse evaporation method developed by Szoka and Papahadjopoulos. See *PNAS USA* 75:4194–4198 (1978). Studies with a variety of plant species (flower and vegetable), like tomato, lily, daylily, onion, peas, petunia and others have been reported. See, Genetic Engineering of Plants, Ed. Kosuge, Merideith and Hollaender, published by Plenum Press, authored by Fraley and Horsch, entitled "In vitro Plant Transformation Systems Using Liposomes and Bacterial Co-Cultivation", Vol. 26, pps. 177–194 (1983) and other articles therein, which are incorporated herein by reference. Phosphatidyl serine-cholesterol (PS-Chol) (an anionic liposome), and other liposomes with encapsulated RNA have been reported. See Fraley et al (above cited). The protocols are reported to be useful to introduce RNA and/or, DNA molecules into the plant protoplasts. In a similar manner, the dispersions of the invention with appropriate adaptation by one skilled in the art to best fit the purpose intended, can be used to transform plants. A cationic lipid of particular interest is 3β[N-(N',N'-dimethyl-aminoethane)-carbamoyl]cholesterol.

A dispersion of the invention containing 3β[N-(N',N'-dimethylaminoethane)-carbamoyl]cholesterol and plasmid DNA is suitable for direct injection into the tumor lesion of a patient. Such a dispersion can be applied as an aerosol into the airways, such as the trachea, the nasal or other cavities of a cystic fibrosis patient. Likewise, such a dispersion may be contemplated for peritonital injection into a patient with ovarian carcinoma with metastasis in the peritonital cavity. For the treatment of neurological diseases like Alzheimer disease, direct injection and transfection of brain cells to cause expression of a therapeutic copy of the defective target gene is of major interest. The dispersions of the invention are likewise considered useful for gene therapy of muscular dystrophy, hemophilia B and several other diseases caused by defective genes.

Instead of a dispersion containing the cationic lipid identified above, the dispersion may contain one or more of the cationic lipids of the invention. It is not excluded to use other cationic lipids with one or more cationic lipids of the invention, providing the formulation is adequately stable and effective for cell transfection. One skilled in the art with the knowledge of the properties of the cationic lipids of the invention (and with the knowledge of the other lipids) can readily formulate a dispersion best suited for the particular cell transfection desired.

In order to facilitate a further understanding of the present invention, the following Examples are given primarily for the purposes of illustrating certain more specific details thereof.

MATERIALS

Cholesterol (99+% grade), cholesterol hemisuccinate, 1,1'-carbonyldimidazole, were purchased from Sigma Chemical Co., St. Louis, Mo. Magnesium powder-50 mesh (99+%), thionyl-bromide (97%), 1,3-propane sulfone (99%), iodomethane (99%), trans-1,2-dichloroethylene (98%), M,M-dimethylaniline (99%), N,N-dimethylethylenediamine (95%), 1,3-bis-dimethylamino-2-propanol (97%), 2-{[2-(dimethylamino)ethyl]methylamino}ethanol (98%), were obtained from Aldrich Chemical Co., Milwaukee, Wis. Cholesteryl chloroformate (95%), and polyethyleneimine were obtained from Fluka. Methanol, dichloromethane, and acetonitrile were HPLC grade solvents. All other chemicals and solvents, unless specified were reagent grade.

A synthetic scheme for cholesteryl carboxylate analogues is shown in FIG. 1.

EXAMPLE 1

Cholesteryl Bromide (I)

Cholesterol, (25 g, 64.6 mmol) was dissolved in 10 ml of dimethylaniline (78.9 mmol) and 5 ml of chloroform. While stirring on ice; small quantities of thionyl bromide (6 ml, 77.6 mmol) dissolved in 20 ml of cold chloroform was added slowly over a period of 15 minutes. After the addition of thionyl bromide was complete, the mixture was stirred for an additional 2 hours at room temperature. The resulting solution was poured into 200 ml of ice cold 95% ethanol and left on ice for 2 hour until crystallization was complete. The product was filtered and washed with 25 ml of ice cold 95% ethanol. A small amount of product was recovered from the filtrate with the addition of 75 ml distilled water followed by refrigeration. Finally, the product was recrystallized from 120 ml of acetone giving 21.8 g of cholesteryl bromide (yield, 75%) with a melting point of 93–95% C. (lit 97–98° C.). The identity of the product was confirmed with mass spectrometry (EI) which showed an intense peak with an m/z of 448, corresponding to the molecular ion ($M^{+\circ}$) of cholesteryl bromide. Also, the bromide molecular weight pattern characteristic of the two different isotopes of bromine (79Br:81Br,1:1) was observed.

EXAMPLE II

Cholest-5-ene-3β-Carboxylic Acid (II)

The synthesis of cholesteryl-3β-carboxylate was performed using a Grignard reaction. All glassware was oven dried at 110° C. overnight. In a 500 ml three-neck flask set up for reflux, a solution of methyl magnesium iodide was freshly prepared by treating 9 g of oven dried (110° C.) magnesium powder in 100 ml anhydrous diethyl ether with 10 ml of methyl iodide. After the vigorous reaction subsided, cholesteryl bromide (25 g, 56 mmol) dissolved in 100 ml of anhydrous diethyl ether was slowly added to the methyl magnesium iodide solution over a three hour period. The solution was refluxed for 36 hours with enough heat required to bring the diethyl ether to a boil. Subsequent to cooling, the Grignard reagent was added to finely ground solid carbon dioxide, and after 1 hour, the complex was hydrolyzed by treatment with ice cold 1 M sulfuric acid. After the steroid was extracted with diethyl ether (3×250 ml), the ethereal layer was washed with 10 mM sodium thiosulfate (3×50 ml) to remove a persistent orange color. After removing the water layer, the ether layer was washed with distilled water and filtered to remove an insoluble residue. The ether layer was subsequently dried over anhydrous sodium sulfate and rotary evaporated to give a white-yellow oily suspension. Titration with pentane yielded 8.6 g of cholesteryl-3β-carboxylate (yield, 37%) as a fine powder with a melting point of 212–215° C. (lit 218–220° C.). Mass spectrometry (EI) showed an m/z of 414 of the molecular ion ($M+^{\circ}$). The product was characterized by 21 proton NMR. The product was lyophilized overnight to give an anhydrous starting material for acylation reactions.

EXAMPLE III

Cholesteryl-3β-Carboxyamidoethylenedimethylamine (III)

The acylation of cholesteryl carboxylate was carried out under a dry argon or nitrogen atmosphere in oven dried glassware. Cholesterol carboxylate (2 g, 4.8 mmol) was suspended in 5 ml of dichloromethane (HPLC grade under 4 Å molecule sieves). A 1.5 molar excess of 1,1'-carbonyldimidazole (CDI, 1.2 g) dissolved in 15 ml dichloromethane was added to the cholesteryl carboxylate suspension is small volumes with intermittent shaking. When the reaction subsided, the solution was stirred overnight. N,N-dimethylethylenediamine (5 ml, 43.2 mol) was subsequently added and the resulting solution was stirred for 36 hours at room temperature. Dichloromethane was removed by rotary evaporation, after which the reaction was quenched with a small volume of distilled water. The acylated steroid was extracted with diethylether (4×50 ml). Subsequently, the pooled ether fractions were back extracted with distilled water (3×50 ml), dried over anhydrous sodium sulfate, and rotary evaporated under reduced pressure. The residue was then triturated with pentane and the product collected on a sintered glass funnel. A voluminous powder (1.7 g, 73% yield) was obtained and found to be pure by TLC (Rf=0.72) using chloroform:methanol:water (65:25:4,v/v/v) as the developing solvent. The product gave a melting point of 167–169° C. Mass spectrometry (FAB+) showed an intense peak at an m/z of 485 which corresponds to the protonated molecular ion $(M+H)^{+\circ}$. The product was characterized by proton NMR.

EXAMPLE IV

Cholesteryl-3β-Carboxyamidoethylenetrimethylammonium Iodide (IV)

The quaternization of Compound III was performed using methyl iodide and potassium bicarbonate. Briefly, 1 g (2.1 mmol) of compound III was dissolved in 40 ml of methanol in the presence of 2 g (20 mmol) of potassium bicarbonate and 2 ml (32.1 mmol) of methyl iodide. The reaction was stirred for 24 hours at room temperature. The solvent was subsequently removed under vacuum and the remaining bicarbonate was neutralized with 1 M HCl until the solution gave a pH reading of 7. Water was removed by lyophilization and the product was extracted from inorganic salt impurities using a small volume of ice cold methanol. After evaporating the solvent, the product was recrystallized from absolute ethanol and was further purified on a reverse phase column using an acetonitrile/0.1% trifluoroacetic acid gradient (100% to 85% acetonitrile in 60 minutes). The powder was shown to be pure with TLC (Rf=0.10) using chloroform:methanol:water (65:25:4 v/v/v) as the developing solvent. It was shown to melt with decomposition at about 190° C., and had a molecular ion with an m/z of 500 $(M^{+\circ})$ according to mass spectrometry (FAB+). The product was characterized by proton NMR.

EXAMPLE V 1,3-Bis-Dimethylamino-2-Propyl-Cholesteryl-3β-Carboxylate (V)

Acylation was performed using CDI activated cholesteryl-3β-carboxylate analogous to the method described for compound III, except that 2,3-bis-dimethylamino-2-propanol (8 ml, 47.6 mmol) was the nucleophile. After the addition of the nucleophile, the reaction was stirred at room temperature for 72 hours. The dichloromethane was removed and the remaining oily residue was dissolved in chloroform. Impurities precipitated with a large volume of petroleum ether (bp, 35–60° C.). The filtrate was rotary evaporated to dryness, re-dissolved in pentane, and filtered once again. After drying, the pentane soluble material was dried and re-dissolved in a small volume of diethyl ether and added to a large volume of hot diethyl ether:acetonitrile (30:70, v/v). The product crystallized at −20° C. after allowing some of the ether to evaporate. Mass spectroscopy (FAB+) gave an m/z of 543 for the protonated molecular ion $(M+H)+^\circ$. The product was characterized by proton NMR.

EXAMPLE VI

1-Dimethylamino-3-Trimethylammonio-DL-2-Propyl Cholesteryl Carboxylate Iodide Salt (VI)

The methoidide of compound V was prepared by gently refluxing compound V (0.5 g, 0.9 mmol) and methyl iodide (2 ml, 32.1 mmol) in 20 ml of ethanol for one hour. After cooling, the precipitate (0.5 g, yield 79%) was recrystallized twice from absolute methanol. The product melted with decomposition at about 232° C. and ran as a single spot on a TLC plate (Rf=0.22) using chloroform:methanol:water (65:25:4, v/v/v) as the developing solvent. The product had a molecular ion with an m/z of 557 $(M^{+\circ})$ with FAB+ mass spectroscopy, consistent with the alkylation of one of the possible two tertiary amine sites. The product was characterized by proton NMR.

EXAMPLE VII

Cholesteryl-3β-Carboxyamidoethyleneamine (VII)

To a solution of ethylenediamine (5.11 g, 85 mmol) in 20 ml dichloromethane, a solution of CDI activated cholesteryl carboxylate (0.7 g, 1.7 mmol) in 5 ml of dichloromethane was added dropwise over a 1.5 hour period. When the addition of the activated sterol was complete, the[]reaction was stirred for 48 hours under nitrogen. After removing the solvent under reduced pressure, the residue was dissolved in chloroform:methanol (2:1, v/v) and extracted against water (3×50 ml). The chloroform phase was subsequently dried with anhydrous sodium sulfate, the solvent removed and the residue purified by preparative TLC using chloroform:methanol:water (65:25:4, v/v/v) as the developing solvent. The band at about Rf=0.3 was collected, extracted with chloroform:methanol (1:1, v/v) and dried under reduced pressure. The product (0.65 g, yield, 81%) ran as a single spot (Rf=0.33) and melted with decomposition at about 194° C. Mass spectrometry (FAB+) gave an m/z of 457 for the protonated molecular ion (M+H)+. The product was characterized by proton NMR.

Figure 2:
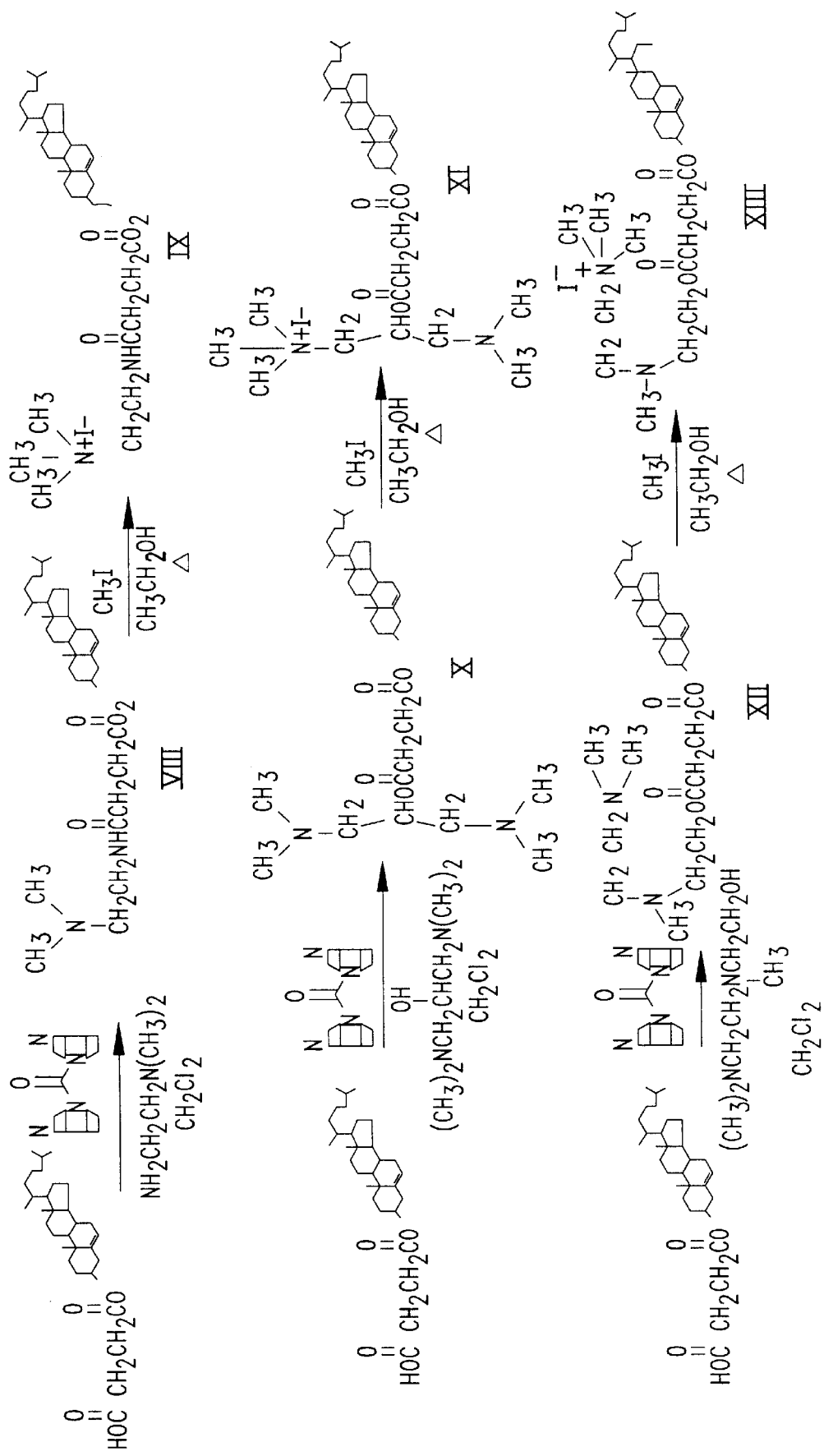
FIG. 2 is the synthetic scheme for cholesteryl hemisuccinate analogues.

A scheme describing the various steps for producing cholesterol hemisuccinate analogues is depicted in FIG. 2.

EXAMPLE VIII

Cholesteryl-3β-Oxysuccinamidoethylenedimethylamine VIII

The synthesis of compound VIII first required the acyl imidazoline of cholesteryl hemisuccinate which was prepared by reacting cholesterol hemisuccinate with N,N-carbonyldiimidazole (CDI) as described for the synthesis of compound III. Briefly, to cholesterol hemisuccinate (2 g, 4.1 mmol) suspended in 5 ml of dichloromethane was added 1.5 equivalents of CDI (1 g) dissolved in 15 ml of dichloromethane. The solution was stirred overnight after which N,N-dimethylethylenediamine (5 ml, 43.2 mmol) was added. Dichloromethane was subsequently removed by rotary evaporation, distilled water was added and the acylated sterol was extracted with diethyl ether (4×50 ml). Subsequently, the ether fractions were washed with distilled water (3×50 ml) and dried over anhydrous sodium sulfate. The ether was removed by rotary evaporation. The product was washed with 200 ml of pentane, and minor impurities were removed using preparative silica gel TLC. After developing with chloroform:methanol:water (65:25:4), v/v/v) the band present at about an Rf=80 was collected and extracted with chloroform/methanol (2:1 v/v). The residue was purified further using chloroform:ethyl acetate (1:1, v/v) as the second developing solvent. The band at about Rf=0.2 was extracted with chloroform/methanol (2:1 v/v). The lyophilized product ran as a single spot on TLC with an Rf of 0.75 using chloroform:methanol:water (65:25:4, v/v/v) as the developing solvent and had a melting point of 119–111° C. Mass spectrometry (FAB+) showed an m/z of 557 which would correspond to the protonated molecular ion $(M+H)^{+\circ}$. The product was characterized by proton NMR.

EXAMPLE IX

Cholesteryl-3β-Oxysuccinamidoethylenetrimethylammonium Iodide (IX)

The quaternization of compound VIII was carried out with methyl iodide in absolute ethanol as described earlier for the synthesis of compound VI. Allowing the solution to cool to room temperature afforded 0.5 g (80% yield) of the quaternary ammonium salt. Subsequently, the product was recrystallized from absolute ethanol giving a fine white powder which melted with decomposition at about 196° C. The product ran as a single spot on a TLC plate (R=0.43) using chloroform:methanol:water (65:25:4) as the developing solvent. Mass spectrometry (FA+) indicated a molecular ion with an m/z of 572 $(M^{+\circ})$. The product was characterized by proton NMR.

EXAMPLE X 1,3-Bi-Dimethylamino-2-Propyl-Cholesteryl-3β-Oxysuccinate (X)

Acylation was performed using CDI activated cholesteryl hemisuccinate according to the procedure described earlier for compound V. After the addition of 1,3-bi-dimethylamino-2-propanol (7 ml, 41.6 mmol), the mixture was stirred for 72 hours, after which the solvent was removed under vacuum. The product, extracted from the residue with diethyl ether (3×75 ml), gave an oil following removal of the ether. The addition of pentane precipitated additional impurities; after rotary evaporation, the resulting oil could not be successfully crystallized using a variety of solvents or by lyophilization. Mass spectrometry (FA+) indicated a protonated molecular ion with an m/z of 616 $(M+H)^{+\circ}$. the product was characterized by proton NMR.

EXAMPLE XI

1-Dimethylamino-3-Trimethylammonio-DL-2-Propyl-Cholesteryl-3β-Oxysuccinate Iodide Salt (XI)

Methylation of compound X was performed using the method described previously (Example VI). After 1 hour, the solution was cooled and the methodide recrystallized twice from absolute methanol to give needle shaped crystals which melted with decomposition at about 222° C. The product ran as a single spot on a TLC plate (R=0.17) using chloroform:methanol:water (65:25:4, v/v/v) as the developing solvent. Mass spectrometry (FA+) indicated a molecular ion with an m/z of 629 $(M^{+\circ})$ consistent with the methylation of 1 of a possible 2 tertiary amine sites. The product was characterized by proton NMR.

EXAMPLE XII

2-{[2-(dimethylamino)ethyl]methylamino}ethyl-Cholesteryl-3β-Oxysuccinate (XII)

The synthesis of compound XII was analogous to the method described for the acylation of compound VIII except that 2-{[2-dimethylamino)ethyl]-methylamino}ethanol (7 ml, 42.0 mmol) was the amino alcohol used as the nucleophile. After extraction with diethylether, the product was lyophilized dry and further purified by preparative TLC using chloroform:methanol:water (65:25:4, v/v/v). After the band present at R=0.80 was collected and extracted with chloroform:methanol, (2:1, v/v), the residue was purified further using chloroform:ethyl acetate (1:1; v/v) as the second TLC developing solvent. The band which was present at about Rf=0.2 was collected and the silica was extracted with chloroform:methanol (2:1, v/v). The product, which ran as a single spot on a TLC plate (Rf=0.72) using chloroform:methanol:water (65:25:4 v/v/v) as the developing solvent gave a melting point of 50–52° C. Mass spectrometry (FA+) showed a protonated molecular ion with an m/z of 615 $(M+H)^{+\circ}$. The product was characterized by proton NMR.

EXAMPLE XIII

2-{[2-Trimethylammonio]ethylmethylamino}ethyl-Cholesteryl-3β-Oxysuccinate Iodine Salt (XIII)

The acylation of compound XII (0.5 g, 0.8 mmol) was carried out under reflux conditions with methyl iodide in absolute ethanol as described in Example VI. The precipitate was recrystallized twice from absolute methanol and stained as a single spot on a TLC plate (Rf=0.22) using chloroform:methanol:water (65:25:4; v/v/v) as the developing solvent. The crystals melted with decomposition at about 172° C. Mass spectrometry (FA+) gave an m/z of 629 for the molecular ion $(M^{+\circ})$ consistent with the methylation of only one the possible two tertiary amine sites. The product was characterized by proton NMR.

Figure 3:
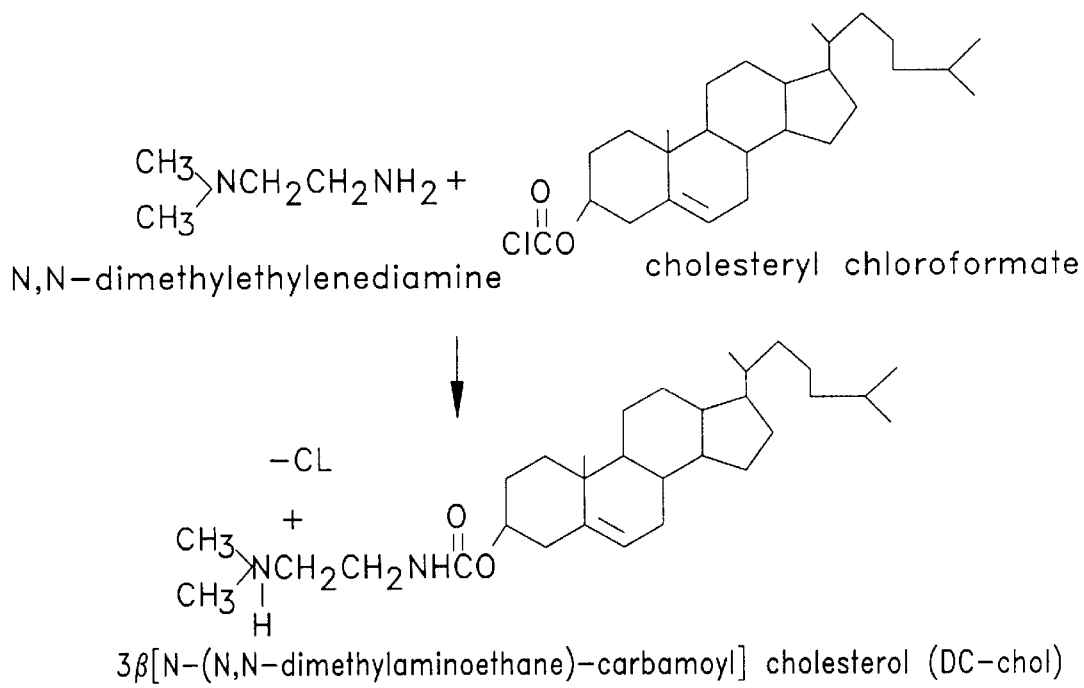
FIG. 3 is the synthetic scheme for cholesteryl formate analogues.

The scheme for the synthesis of cholesteryl formate analogues is shown in FIG. 3.

EXAMPLE XIV

3β[N-(N',N'-dimethylaminoethane)-carbamoyl] cholesterol (XIV)

Compound XIV was synthesized by mixing a solution of cholesteryl chloroformate (0.5 mmol) in chloroform with a solution of N,N-dimethylethylenediamine (9.1 mmol) in chloroform in a dry ice-ethanol bath. The solvent and the unreacted amine were removed in vacuo. Compound XIV was purified by two successive recrystallizations in ethanol. (Yield, 65%) TLC (chloroform:methanol=65:35) showed a single spot (Rf=0.37) when developed with iodine. The product was characterized by proton NMR.

EXAMPLE XV

3β[N-(polyethyleneimine)-carbamoyl]cholesterol XV)

Synthesis of compound XV was similar to that of compound XIV. Cholesterol chloroformate (0.1 mmol) and polyethyleneimine 600 (6 g) were mixed in chloroform in a dry ice-ethanol bath. After the volatile material of the reaction mixture was removed in vacuo, the solid crude product was dialyzed against 4L distilled water for 3 days (during which the water was changed several times). Finally, the product was lyonhilized to dryness, giving an estimated yield of 81%. Compound XV ran as a single spot on TLC (chloroform:methanol=65:35).

EXAMPLE XVI

Preparation of Cationic Livid Dispersions

The cationic cholesterol derivatives of the invention were mixed with a phospholipid co-lipid in chloroform solution at different molar ratios. The solvent was removed by evaporation under a stream of $N_2$ gas and desiccated in vacuo for at least 30 minutes. The dry lipid film was hydrated in 20 mM Hepes buffer, pH 7.8, overnight. The suspension was sonicated in a bath-type sonicator (Laboratory Supplies, Hicksville, N.Y.) to generate small particle dispersions (average diameter=150 nm). The co-lipid is phosphatidylethanolamine.

EXAMPLE XVII

Transfection of Cells

Plasmid pUCSV2CAT (approximately 5 kb in size) containing the structural gene of *E. coli* chloramphenicol acetyl transferase (CAT) driven by the SV40 virus early promoter was used as a model for the polyanions to be delivered by the cationic lipid dispersions. DNA was mixed with the cationic lipid dispersions of the invention in 1 ml serum-free M199 medium or McCoy's medium to form DNA/lipid complex. Cultured mammalian cells of about 80–100% confluency in a 6-well plate were washed once with serum-free medium. The DNA/lipid complex was added to the washed cells which were incubated at 37° C. for 5 hours. The cells were washed again and the serum-containing medium was added. Cells were harvested 30–72 hours later and extracted for cellular proteins. The CAT activity in the extracted protein was measured by using either [$^{14}$C] chloramphenicol or [$^{3}$H] acetyl CoA as a radiolabeled substrate. One activity unit of CAT is defined as nmole of radiolabeled substrate converted to the radiolabeled product in one minute. Protein content in the cell extracts was measured by the Bradford (BIORAD) assay.

EXAMPLE XVIII

Isolation of Protein Kinase C

As rapidly as possible, brains for 25 Sprague-Dawley rats (150–200 g) were removed, washed with 100 ml of 20 mM TRIS, 1 mM EDTA, 1 mM EGTA, pH 7.5, and homogenized in 150 ml of ice cold 20 mM TRIS, 10 mM EGTA, 2 mM EDTA, 10 mM DTT, 0.25 M sucrose, 2 mM PMSF and 100 μg/ml leupeptin, pH 7.5. The homogenate was immediately centrifuged at.100,000 g for 40 minutes at 4° C. in a Beckman Ti 50.2 rotor. The supernatant was applied to a 2.5×20 cm column of DEAE Sepharose (fast flow) containing 60 ml of resin equilibrated with 20 mM TRIS, 1 mM EDTA, 1 mM DTT, pH 7.5 (buffer A). The column was washed with 300 ml of buffer A and an additional 200 ml of buffer A containing 0.03 M KCl. Protein kinase C was eluted with a 500 ml continuous KCl gradient (0.03–0.3 M KCl). Fractions of 5 ml volumes were collected. Fractions showing calcium and phospholipid dependence were pooled; the salt concentration was adjusted to 1.5 KCl with the appropriate quantity of solid KCl. The crude sample containing 1.5 M KCl was stirred for 15 minutes and subsequently loaded onto a 1×10 cm column containing 9 ml Phenyl sepharose equilibrated with 1.5 M KCl in 20 mM TRIS, 0.5 mM EGTA, 1 mM DTT, pH 7.5 (buffer B). The column was washed with 90 ml of buffer B containing 1.5 M KCl. PKC was eluted with a 100 ml continuous KCl gradient (1.5–0 M KCl). Fractions of 3 ml volumes were collected. The column was washed with an additional 50 ml of buffer B. Most of the enzyme activity eluted during this stage. Fractions showing calcium and phospholipid dependence were pooled and concentrated to 4 ml using an Amicon ultrafiltration cell fitted with a YM-10 filter. The concentrated sample was loaded onto a 2.5×100 cm column containing 400 ml of Sephacryl S-200 HR beads equilibrated with buffer B containing 10% glycerol (buffer C). Fractions of 3 ml volumes were collected. About 150 ml of buffer was run through; PKC eluted very close to the column void volume. The fractions showing calcium and phospholipid dependence were pooled and loaded onto a 0.5×5 cm column containing 2.5 ml polylysine agarose equilibrated with buffer C. PKC was eluted with a 40 ml continuous KCl gradient (0–0.8 M KCl). Fractions of 1 ml volumes were collected. The first few active fractions were contaminated. The uncontaminated fractions were pooled, concentrated, and diluted with buffer C to remove the high salt content. After reconcentrating, the sample was divided into working portions, frozen in liquid nitrogen and stored at −80° C. Full activity was regained after rapid thawing. Trace impurities (116 k, 66 k, and 50 k Mr) could still be detected when the gel was silver stained heavily. The enzyme gave a specific activity of 200 nmoles phosphate incorporated per minute per milligram of protein when assayed for histone phosphorylation using the Triton mixed micelle assay with 6.5 mole % phosphatidylserine, 2.5 mole % DAG and 100 μM calcium present. Specific activities ranging from 30 nmoles/min/mg to 600 nmoles/min/mg have been observed for PKC using the Triton mixed micelle assay under the same conditions.

The DNA was mixed with the cationic lipid dispersion containing the co-lipid (DOPE) and 3β[N-(N',N'-dimethylaminoethane)-carbamoyl]cholesterol and transfection is performed as shown in Example XXII.

Similar mixtures are obtained with other dispersions containing a selected co-lipid and other cationic lipids of the preferred group described above like cholesteryl-3β- carboxamidoethylenetrimethylammonium iodide, cholesteryl-3β-carboxyamidoethylenamine, cholesteryl-3β-oxysuccinamidoethylenetrimethylammonium iodide, and 3β-[N-(polyethyleneimine)-carbamoyl]cholesterol. Transfection of the mammalian cells was performed as shown below in Example XXII or by protocols referred to above.

EXAMPLE XIX

Mixed Micelle Assay of Protein Kinase C

Phosphatidylserine and 1,2-diolefin with and without additive were dissolved in a solution of chloroform/methanol (2:1, v/v). Solvent was evaporated with a stream of nitrogen and last traces removed using a vacuum desiccator at 40° C. The lipid films were then solubilized by the addition of 3% Triton X-100, vortexed vigorously for 30 seconds and then incubated at 30° C. for 10 minutes to allow for equilibration. At 25 μl, an aliquot of this solution was used in a final assay volume of 250 μl, containing 20 mM TRIS-HCl, pH 7.5, 10 mM $MgCL_2$, 200 μg/ml histone III-S, 100 μM $CaCl_2$, 10 μM[γ-$^{32}$P] adenosine 5' triphosphate, 2.75 mM Triton X-100, with 300 μM (6.5 mole percent) phosphatidylserine and 107 μM (2.5 mole percent 1,2-diolefin. For controls, 25 μl of 20 mM EGTA replaced the $CaCl_2$. To initiate the reaction, 150 ng of protein was added. After briefly mixing, the tubes were incubated for 10 minutes at 30° C. The reaction was terminated by adding 1 ml of cold 0.5 mg/ml BSA and 1 ml of cold 25% trichloroacetic acid. This mixture was passed through a GF/C Whatman filter and washed five times with 2 ml of 25% trichloroacetic acid. After drying, the filters were counted with 6 ml ACS scintillation fluid.

EXAMPLE XX

Formation of Homogenous Dispersion with Cationic Cholesterol Derivatives

None of the cationic cholesterol derivatives by themselves form stable homogenous dispersion by sonication in a low ionic strength buffer. When stable dispersions are desired, it was necessary to add an acidic or neutral phospholipid to form mixed lipid dispersion. For example, compound VIII requires a minimal of 1 part of PC or PE and 9 parts of compound VIII to form a uniform dispersion. In the case of compound XIV, a minimal ration of phosphatidyl choline (PC) or phosphatidyl ethanolamine (PE) to XIV=4:6 is required. Such non-cationic lipid used in the dispersion is called co-lipid.

EXAMPLE XXI

Delivery of DNA into Mammalian Cells by Cationic Lipid Dispersions

Plasmid DNA, pUCSV2CAT, was used as a model compound for polyanions because it contains a structural gene for CAT. The efficiency of intracellular delivery can be readily assayed by the expression of CAT activity in the extracted proteins of the treated cells. Table 1 lists the CAT activity of mouse L929 cells which have been transfected with this plasmid DNA as mediated by various cationic lipid dispersions. In addition, the inhibitory activity of the pure cationic cholesterol derivatives on diolefin, phosphatidyl serine (PS), and $Ca^{2+}$stimulated protein kinase C was also measured. This activity was expressed as an $IC_{50}$, which is the concentration at which 50% of PKC activity was inhibited. As can be seen from Table I, derivatives giving low $IC_{50}$ values, i.e., those strong PKC inhibitors, were not a good delivery vehicle for DNA. For example, compounds IV, XI, VI and XIII, all having a $IC_{50}$ value less than 20 μM, produced minimal CAT activities in the treated cells. Among the ones which gave rise to high CAT activities, derivatives with a single tertiary amino group (compounds VIII, VI and III) were more effective in delivering DNA than similar analogs containing a single quaternary amino group (compounds IX and IV). Furthermore, among the derivatives with the same amino head group, those containing a longer spacer arm (compounds VIII and IX) delivered a greater quantity of DNA than those containing a shorter spacer arm (compounds X, XI, V, VI and XV) were generally less effective delivery vehicles.

Compound VII deserves some special attention. It contains only a single primary amino group with a short spacer arm, yet the transfection activity was relatively high.

TABLE I

| Compound | PKC Inhibition $IC_{50}$ (μM) | Relative CAT Activity |
| --- | --- | --- |
| III | 258 | 18 |
| IV | 12 | 0.7 |
| V | 643 | 2 |
| VI | 11 | 1 |
| VII | 246 | 68 |
| VIII | 191 | 100 |
| IX | 59 | 50 |
| X | 408 | 0.5 |
| XI | 15 | 11 |
| XII | 164 | 19 |
| XIII | 20 | 14 |
| XIV | >1,000 | 75 |
| XV | — | 11 |

EXAMPLE XXII

The Importance of the Co-lipid

Figure 4:
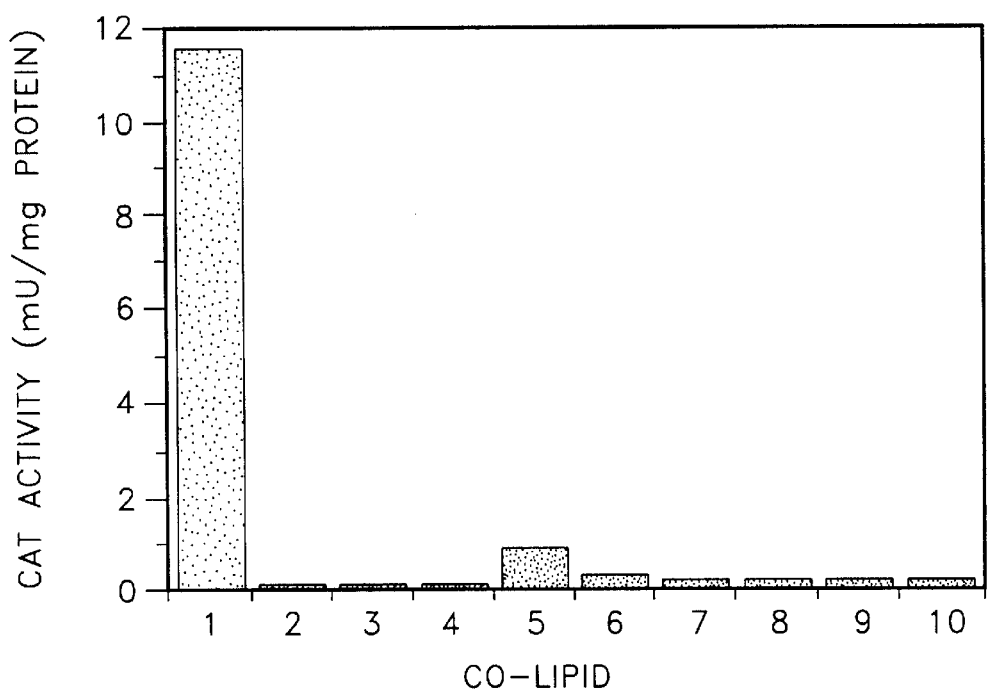
FIG. 4 is a graph of the effect of different co-lipids on the transfection activity of a cationic lipid dispersion in L929 cells.

The experiments described in Example XXI were done with a lipid dispersion containing a cationic cholesterol derivative and a co-lipid dioleoyl phosphatidylethanolamine (DOPE). We have studied the role of co-lipid in the delivery efficiency. FIG. 4 shows the data of an experiment in which compound VIII was mixed with a variety of different co-lipid, neutral and acidic, at a molar ratio of 1:1. The DNA delivery activity of these mixed dispersions were then studied. As can be seen, only DOPE supported the delivery activity of compound VIII. Other neutral lipids such as dioleoyl phosphatidylcholine (DOPC), N-methyl-DOPE, N,N-dimethyl DOPE had little or no activity. None of the acidic lipids, such as PS and phosphatidylglycerol (PG) showed any activity.

Figure 5:
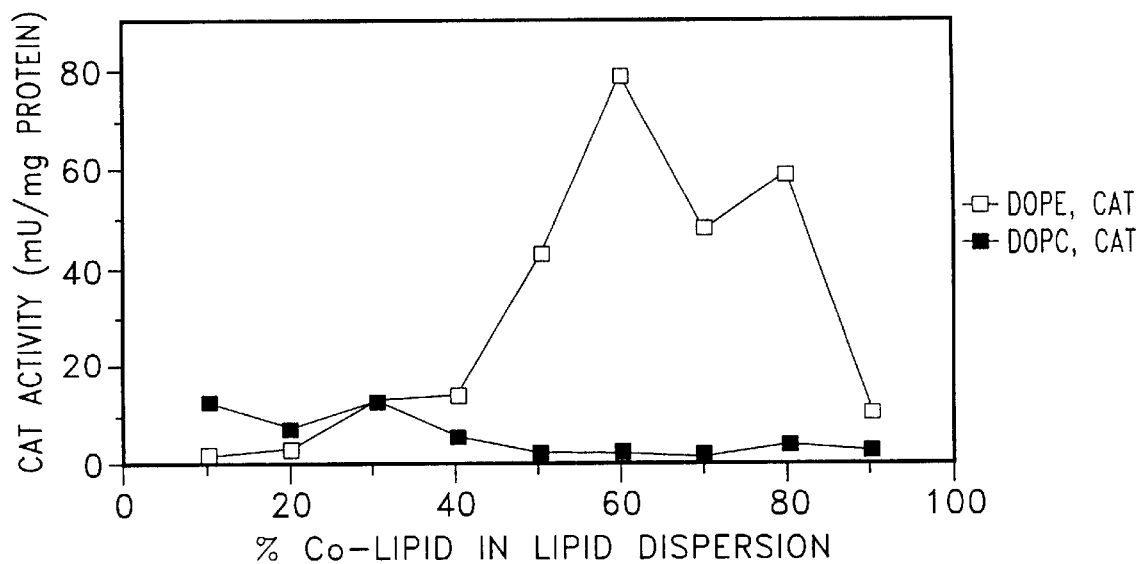
FIG. 5 is a graph of the effect of the ratio of co-lipid to a cationic lipid of the present invention on the transfection activity in L92.9 cells.

The molar ratio of Dope and compound VIII in the dispersion also played an important role. FIG. 5 shows that maximal DNA delivery activity of the dispersion occurred when the dispersion contained 20–50% compound VIII. Too much or too little of compound VIII in the mixed dispersion did not yield good delivery activity.

EXAMPLE XXIII

Optimization of Dispersion-to-DNA Ratio for Delivery

Figure 6:
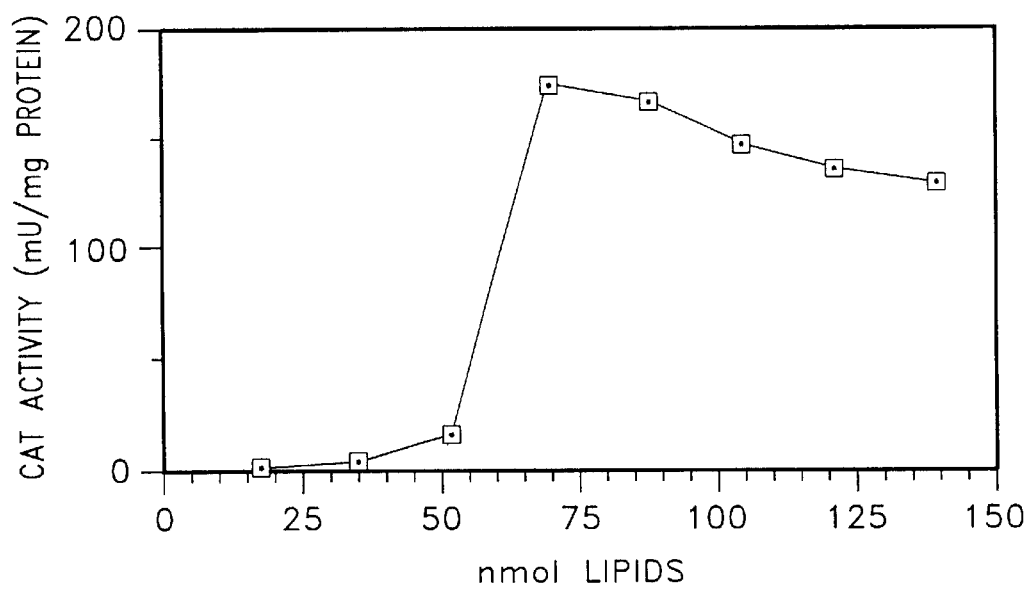
FIG. 6 is a graph of the effect of lipid dose on the transfection activity in L929 cells.
Figure 7:
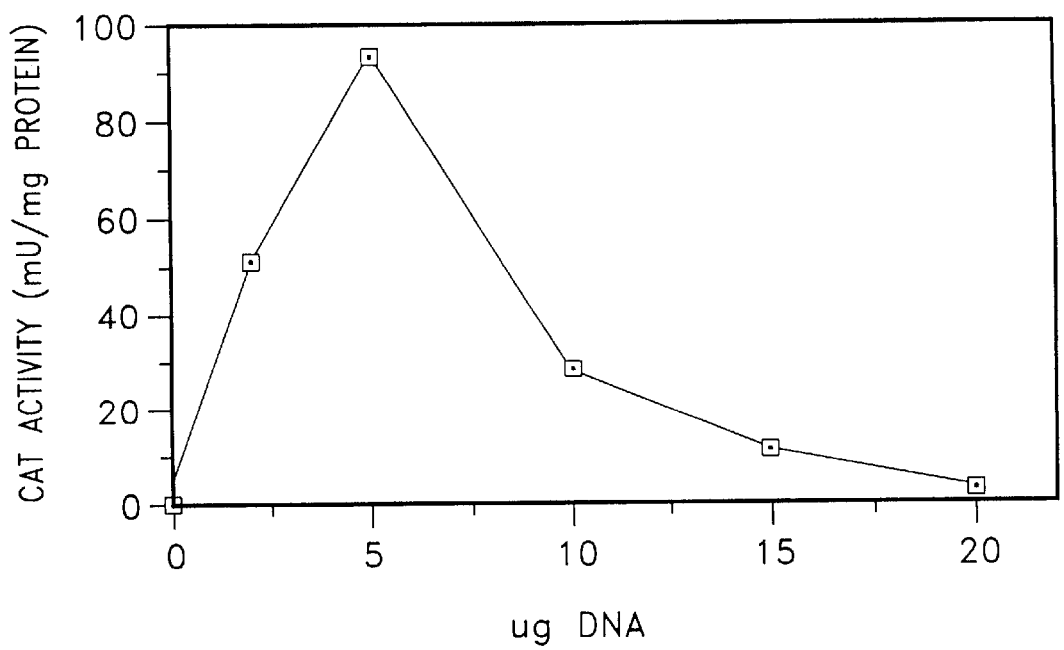
FIG. 7 is a graph of the effect of DNA dose on the transfection activity of the lipid dispersion in L929 cells.

A 1:1 mixture of compound VIII and DOPE were used to study the optimal ratio of dispersion-to-DNA for delivery. FIG. 6 shows the data of an experiment in which various amounts of dispersion were added to a fixed amount of DNA (5 μg) for transfection. Maximal activities occurred at 69–80 nmoles of dispersion. We then used 70 nmoles dispersion and varied the amount of DNA for transfection (FIG. 7). The bell-shaped curve in the figure indicates that a 5 μg DNA gave the maximal activity. Thus the optimal ratio of dispersion-to-DNA was 70 nmole lipid for 5 μg DNA.

EXAMPLE XXIV

Complex Formation of DNA with Cationic Lipid Dispersions

Figure 8:
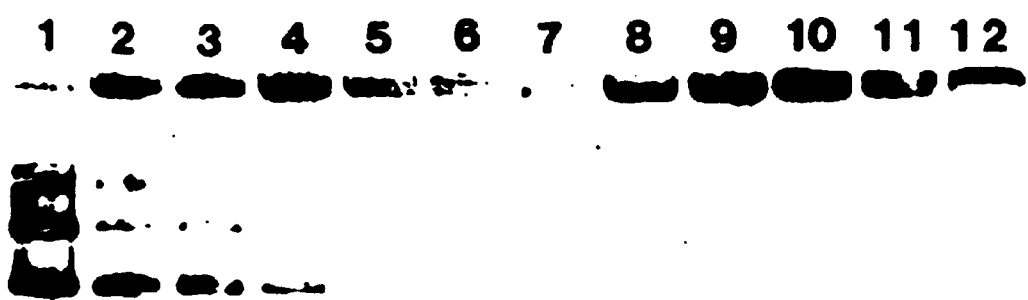
FIG. 8 is a representation of a gel showing complex formation of DNA with the cationic lipid dispersion.

It was expected that polyanions were complex with the cationic lipid dispersion via electrostatic interactions. Again, a 1:1 mixture of compound VIII and DOPE was used for the study. We have characterized the dispersion/DNA complexes by agarose gel electrophoresis. As shown in FIG. 8, 1 μg plasmid DNA electrophoresed as two closely located bands in the gel (lane 1), which could be completely digested if DNAse was included in the incubation buffer (lane 7). Incubation mixtures containing increasing amounts of dispersion showed decreasing intensities of DNA bands (lanes 2, 3, 4, 5 and 6). Furthermore, all of the uncomplexed, free DNA could be digested by DNAse, but only a portion of the complexed DNA was digested (lanes 8, 9, 10, 11 and 12). These results clearly showed that the lipid dispersion form complexes with DNA which are either larger in size and/or less negatively charged such that the complex does not enter the gel during electrophoresis. Furthermore, the complex is partially resistant to DNAse, whereas the free, uncomplexed DNA is not. It should be noted that at the optimal dispersion/DNA ration nearly all DNA were complexed with liposomes (not shown in FIG. 8).

EXAMPLE XXV

Figure 9:
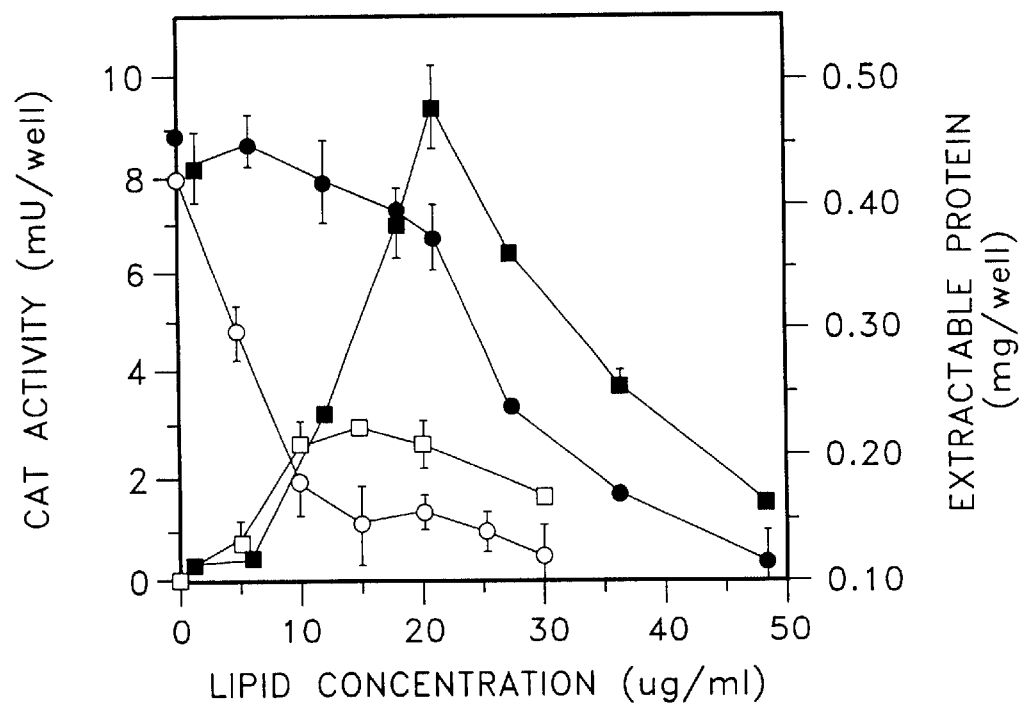
FIG. 9 is a graph of the transfection efficiency and toxicity of a cationic lipid of the present invention.

Relationship Between Delivery Activity and Cytotoxicity of the Cationic Lipid Complex This was studied by using a dispersion composed of compound XIV and DOPE (3:2, molar ratio). A431 human epidermoid carcinoma cells were used for the transfection experiments. A fixed amount of DNA (4 μg) was mixed with an increasing amount of cationic lipid dispersion or a commercially available transfection reagent, Lipofectin, and added to the A431 cells for transfection (FIG. 9). The toxicity of the treatment to the cells was measured as the total amount of cellular protein extractable at the time of CAT activity assay. As can be seen from the Figure, Lipofectin treated cells showed a greatly reduced protein content with 50% inhibition occurring at about 7 μg lipid/ml. Cells treated with the dispersion containing compound XIV and DOPE showed less toxicity; the $IC_{50}$ occurred at about 25 μg lipid/ml. The novel cationic cholesterol dispersion had also produced higher CAT activities than.Lipofectin.. It is important to note that maximal CAT activity of cells treated with Lipofectin occurred at the Lipofectin concentration of 15 μg/ml. At this concentration only about 12% of the total cellular proteins could be recovered from the culture. On the other hand, maximal CAT activity of cells treated with the cationic cholesterol dispersion occurred at 20 μg/ml; about 80% of the total cellular protein still remained in the culture at this concentration. Thus, the novel cationic cholesterol dispersion is more potent in the delivery activity and is also less toxic to the treated cells.

EXAMPLE XXVI

Stability of the Cationic Cholesterol Derivatives

Lipid dispersions were prepared with various cationic cholesterol derivatives and DOPE (about 1:1 molar ratio). The transfection activities of the dispersions were tested at different times after the dispersions were stored at 4° C. in PBS, pH 7.5. Of the derivatives listed in Table 1, only the dispersions containing compounds XIV and XV were stable after storage; their transfection activities did not change for at least 2 months. On the other hand, the dispersions composed of other derivatives lose activity after 2–3 days in storage. Compounds XIV and XV contain a carbamoyl linker bond whereas other compounds contain either an ester bond or an amide bond. It is known that ester and amide bonds are more sensitive than the carbamoyl bond to hydrolysis particularly in the presence of bases. The cationic derivatives may catalyze the hydrolysis of each other's ester bonds, leading to the inactivation of the delivery activity. Compounds containing carbamoyl linker bonds are less sensitive to the base-catalyzed hydrolysis, yet they can still be hydrolysed by cellular enzymes, i.e., they are biodegradable. This is in contrast to the non-degradable ether bond in DOTMA which is the active ingredient of Lipofectin. Thus, a carbamoyl bond seems to be the best choice for the linker bond of the cationic lipids as a delivery vehicle for polyanions.

Various of the features of the invention which are believed to be new are set forth in the appended claims.

We claim:

1. A substantially non-toxic biodegradable amine derivative of cholesterol having a cholesteryl group, a —NH—(CO)—O—* linker, which linker is linked by the side marked by the asterisk to the 3 position of the cholesteryl group and by the other side via the nitrogen to a spacer, the spacer having 1 to 15 carbon atoms in a branched or linear hydrocarbon, which is linked on its other side to a tertiary amino group.

2. A derivative of cholesterol of claim 1 wherein the spacer is —$(CH_2)_2$—.

3. A cationic lipid of the derivative of cholesterol of claim 1.

4. A dry lipid film of the derivative of cholesterol of claim 3.

5. A hydrated lipid film of the derivative of cholesterol of claim 4.

6. A substantially non-toxic biodegradable amine derivative of cholesterol which is 3β[N-($N^1$-$N^1$-dimethylaminoethane)carbamoyl]cholesterol.

7. A cationic lipid of the derivative of cholesterol of claim 6.

8. A crystalline product of the derivative of cholesterol of claim 6.

9. A dry lipid film of the derivative of cholesterol of claim 6.

10. A hydrated lipid film of the derivative of cholesterol of claim 9.

11. A substantially non-toxic biodegradable derivative of cholesterol which is 3β[N-(polyethyleneimine)-carbamoyl] cholesterol.

12. A cationic lipid of the derivative of cholesterol of claim 11.

13. A lyophilate of the derivative of cholesterol of claim 9.

14. A substantially non-toxic biodegradable amine derivative of cholesterol having a cholesteryl group, a linker selected from the group consisting of a —NH—(CO)—* and a —O—(CO)—* (reverse ester) linker, which linker is linked by the side marked by the asterisk to the 3 position of the cholesteryl group and by the other side via the nitrogen or the oxygen, respectively, to a branched or linear hydrocarbon spacer having 1 to 15 carbon atoms, which is linked on its other side to an amino group selected from the group consisting of a primary, tertiary or quaternary groups.

15. A derivative of cholesterol of claim 14, wherein the spacer is of 2 to 3 carbon atoms.

16. A derivative of cholesterol of claim 15 wherein the spacer is —(CH$_2$)$_2$—.

17. A substantially non-toxic biodegradable amine derivative of cholesterol of claim 14 wherein the linker is a —NH—(CO)—* linker, and the amino group is primary.

18. A derivative of cholesterol of claim 17 which is cholesteryl-3β-carboxyamidoethylamine.

19. A substantially non-toxic biodegradable amine derivative of cholesterol of claim 16, wherein the linker is a —NH—(CO)—* linker and the amino group are selected from the group consisting of one tertiary and one quaternary amino group.

20. A derivative of cholesterol of claim 19 wherein the derivative of cholesterol is selected from the group consisting of cholesteryl-3β-carboxyamidoethylenedimethylamine and cholesteryl-3β-carboxyamidothylenetrimethlammonium iodide.

21. A powder or a lyophilate of a derivative of cholesterol of claim 20.

22. A derivative of cholesterol of claim 20 which is cholesteryl-3β-carboxyamidoethylenedimethylamine.

23. A derivative of cholesterol of claim 20 which is cholesteryl-3β-carboxyamidoethylene-trimethylammonium iodide.

24. A substantially non-toxic biodegradable amine of the derivative of cholesterol of claim 16 wherein the linker is —O—(CO)—*, and the amino group is selected from the group consisting of one tertiary and one quaternary amino group.

25. A derivative of cholesterol of claim 24 wherein the derivative of cholesterol is selected from the group consisting of 1,3-bis-dimethylamino-2-propyl-cholesteryl-3β-carboxylate and 1-dimethylamino-3-trimethylamino-DL-2-propyl cholesteryl carboxylate iodide.

26. A derivative of cholesterol of claim 25, which is 1,3-bis-dimethylamino-2-propyl-cholesteryl-3β-carboxylate.

27. A substantially non-toxic biodegradable amine derivative of cholesterol having a cholesteryl group, a —(CO)—O—* ester linker which a linker is linked by the side marked by an asterisk to the 3 position of the cholesteryl group and by the other side via the carbon to a 5 to 8 carbon atoms branched or linear heteroatom spacer comprising in addition to hydrocarbons, at least one atom selected from the group consisting of oxygen and nitrogen, which spacer is linked on its other side to an amino group consisting of one or two tertiary amino groups or one or two amino quaternary groups.

28. A derivative of cholesterol of claim 26 wherein the spacer has a nitrogen and an oxygen atom.

29. A derivative of cholesterol of claim 27 which is cholesteryl-3β-oxysuccinamidoethylenedimethylamine.

30. A derivative of cholesterol of claim 28 which is cholesteryl-3β-oxysuccinamidoethylenetrimethylammonium iodide.

* * * * *